United States Patent [19]

Wardleworth et al.

[11] Patent Number: 4,933,478

[45] Date of Patent: Jun. 12, 1990

[54] PROCESS FOR THE MANUFACTURE OF ALIPHATYLPHOSPHINIC ACID DERIVATIVES

[75] Inventors: Peter S. Wardleworth, Tyldesley; Eric K. Baylis, Stockport, both of England

[73] Assignee: Ciba-Geigy Corporation, Ardsley, N.Y.

[21] Appl. No.: 239,233

[22] Filed: Sep. 1, 1988

[30] Foreign Application Priority Data

Sep. 11, 1987 [GB] United Kingdom ................. 8721442

[51] Int. Cl.$^5$ ................................................ C07F 9/32
[52] U.S. Cl. ...................................... 558/104; 558/186
[58] Field of Search .......................................... 558/104

[56] References Cited

U.S. PATENT DOCUMENTS 4,656,298  4/1987  Dingwall et al. ...................... 556/12
4,772,738  9/1988  Dingwall et al. ..................... 558/175

OTHER PUBLICATIONS

J. Prakt. Chem., vol. 316, pp. 550-556 (1974).
Derwent Abstract of SU-117449A (1985).
Gallagher et al., Aust. J. Chem., vol. 33, pp. 287-294 (1980).

J. Org. Chem., vol. 26, pp. 4088-4092 (1961).

Primary Examiner—Anton H. Sutto
Attorney, Agent, or Firm—JoAnn Villamizar

[57] ABSTRACT

A process for the production of aliphatylphosphinic acid derivatives, especially of alkyl dialkoxyalkylphosphinates having the formula I

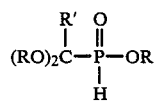

in which R is $C_1$–$C_4$-alkyl and R' is hydrogen or $C_1$–$C_4$-alkyl, comprising reacting, in the presence of an acidic catalyst, aqueous phosphonic acid with the corresponding trialkyl orthoester having the formula II:

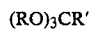

in whicih R and R' have their previous significances, the amount of the orthoester of formula II used being equal to, or in excess of the stoichiometric amount of both water and phosphinic acid present in the aqueous phosphinic acid reactant.

10 Claims, No Drawings

PROCESS FOR THE MANUFACTURE OF ALIPHATYLPHOSPHINIC ACID DERIVATIVES

The invention relates to a novel process for the manufacture of aliphatylphosphinic acid derivatives, especially of alkyl dialkoxyalkylphosphinates having the formula I:

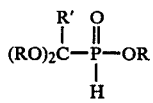   I in which R is $C_1$–$C_4$-alkyl and R' is hydrogen or $C_1$–$C_4$alkyl, comprising reacting, in the presence of an acidic catalyst, aqueous phosphinic acid with the corresponding trialkyl orthoester having the formula II:

   II in which R and R' have their previous significances, the amount of the orthoester of formula II used being equal to, or in excess of the stoichiometric amount of both water and phosphinic acid present in the aqueous phosphinic acid reactant.

Aliphatylphosphinic acid derivatives, especially alkyl dialkoxyalkylphosphinates are useful intermediates for compounds having valuable properties, for instance the pharmaceutically active substituted propane-phosphonous acid compounds described in European Patent Specification No. 0181833.

Various methods have been suggested for the production of alkyl dialkoxymethylphosphinates. For example, Gallagher and Honegger Aust. J. Chem. 1980, 33, 287 describe the production of methyl dimethoxymethylphosphinate or ethyl diethoxymethylphosphinate by adding p-toluene sulfonic acid to anhydrous phosphinic acid followed by trimethyl- or triethyl orthoformate, respectively.

Moreover, Gross and Costisella (J. Prakt. Chem. 1974, 316, 550) have described the reaction of anhydrous phosphonic acid with trialkyl orthoformates to produce dialkyl (dialkoxymethyl) phosphonates. These workers reported that alkylation at phosphorus occurred only when anhydrous acid was used; if anhydrous phosphonic acid was not used, dialkyl phosphonate was the sole product.

Still further, in Russian Patent No. 1174439A, O-alkyl-O-trimethylsilyl dialkoxymethylphosphonites are produced by reacting anhydrous phosphinic acid with trialkyl orthoformate in the presence of p-toluene sulfonic acid; and subsequently reacting the mixture so obtained with bis(trimethylsilyl)amine.

In contrast to this trend in related processes, we have now found that alkyl dialkoxyalkylphosphinates can be produced by reacting trialkyl orthoesters with aqueous phosphinic acid, thereby avoiding the use of anhydrous phosphinic acid which is reported to be potentially hazardous (J. Org. Chem 1961, 26, 4090).

R and R' as $C_1$–$C_4$alkyl may be methyl, ethyl, n-propyl, isopropyl, n-butyl or t-butyl.

Preferred reactants of formula I are those in which each R is methyl or ethyl, in particular those reactants in which each R is ethyl and R' is hydrogen or methyl.

Specific examples of reactants II include:
trimethyl orthoformate,
triethyl orthoformate,
tri-n-propyl orthoformate,
tri-n-butyl orthoformate,
trimethyl orthoacetate,
triethyl orthoacetate,
tri-n-propyl orthoacetate and
tri-n-butyl orthoacetate.

The orthoesters of formula II are known compounds and can be produced e.g. by the method described in "Carboxylic Ortho Acid Derivatives Preparation and Synthetic Applications" Robert H. DeWolfe, Organic Chemistry A Series of Monographs Vol. 14 Academic Press.

The aqueous phosphinic acid reactant used contains 50 to 95% by weight of phosphinic acid, preferably 80 to 95% by weight of phosphinic acid, the rest being water.

An amount of trialkyl orthoester of formula II is employed which is equal to or is in excess of the stoichiometric amount of both water and phosphinic acid present in the aqueous phosphinic acid. In the preferred instance, a stoichiometric excess of trialkyl orthoester is used which serves to remove water in the reaction mixture.

By way of illustration, 1 kg of a 50% w/w aqueous solution of phosphinic acid contains 7.6 moles of phosphinic acid and 27.8 moles of water, and the stoichiometric amount of orthoester required to produce a compound of formula I is 43.0 moles. Analogously, 1 kg of 90% w/w aqueous solution of phosphinic acid contains 13.64 moles of phosphinic acid and 5.56 moles of water, and the stoichiometric amount of orthoester required is 32.84 moles. While there is no theoretical upper limit on the excess amount of orthoester reactant, an amount of up to 10 times, for example, up to 5, such as from approximately 1.0 times to approximately 5 times, such as from approximately 2.2 times to approximately 4.4 times, the stoichiometric amount is generally convenient.

The reaction may be performed in a solvent which is inert under the reaction conditions e.g. methylene chloride, toluene, ethanol or in an excess of orthoester of formula II.

The reaction is conveniently conducted at a temperature within the range of from 0 to 100, preferably 0 to 35 deg. C and under an inert atmosphere at ambient pressure.

The reaction is performed in the presence of an acidic catalyst which may be a Lewis- or Bronsted acid such as a co-ordinatively unsaturated halide of a group IIB, group III or group IV metal, or a mineral acid, alkane- or benzenesulphonic acid or an α-halogenated alkanoic acid, e.g. sulfuric acid, methane- or ethanesulphonic acid, p-toluene sulfonic acid, trifluoracetic acid, or zinc chloride or boron trifluoride or boron trifluoride etherate. The preferred catalyst is boron trifluoride etherate, when R' is $C_1$–$C_4$-alkyl or, when R' is hydrogen, trifluoroacetic acid which provides a cleaner product which is readily purified, e.g. by distillation on a wiped wall molecular still. Generally speaking, a catalytic amount of the acidic catalyst is sufficient. However, it has been shown to be convenient to apply from approximately 0.01 to approximately 0.4, preferably from approximately 0.05 to approximately 0.3, acid equivalents of the acidic catalyst, i.e. from approximately 0.01 to approximately 0.4, preferably from approximately 0.05 to 0.3 moles of a mono-basic Bronsted acid, such as trifluoroacetic acid, per mole of the phosphinic acid used.

The following Examples further illustrate the present invention. Parts and percentages are by weight unless otherwise stated.

In some cases, the yield of product increases to a maximum and then decreases with time. The maximum yield can be obtained by monitoring the course of the reaction and isolating the product when the yield reaches the maximum value. Typically the reaction time may be up to 72 hours.

EXAMPLE 1

(a) Commercially available 50% aqueous phosphinic acid is concentrated by evaporation to constant weight on a rotary evaporator at water pump pressure at a temperature not exceeding 40° C., to provide a solution consisting of approximately 80 parts phosphinic acid and 20 parts water by weight. The proportion of phosphinic acid is determined exactly by titration of a diluted aliquot with standard sodium hydroxide solution.

(b) 412.5 parts of 80% aqueous phosphinic acid solution prepared as described in Example 1a) are dissolved in 2223 parts of triethyl orthoformate under an atmosphere of nitrogen. 114 parts of trifluoroacetic acid are added, dropwise, over ten minutes to the stirred solution. A slight exotherm occurs, the temperature of the reaction mixture rising to about 28°–30° C. The mixture is stirred at ambient temperature unter a stream of nitrogen for 48 to 60 hours until the $^{31}$P-nmr spectrum indicates that the reaction is essentially complete. Evaporation to constant weight on a rotary evaporator, at a bath temperature not exceeding 40° C., and water pump pressure, gives on oily residue. This is dissolved in 4000 parts of dichloromethane and the resulting solution added slowly, with vigorous stirring, to a solution of 358 parts of disodium hydrogen phosphate dodecahydrate dissolved in 3000 parts of water. The organic layer is separated, dried with anhydrous sodium sulphate and evaporated on a rotary evaporator, below 40° C., giving 822 parts of a crude product shown by $-$P-nmr assay to contain 90.6% ethyl diethoxymethyl-phosphinate. The crude product is purified by distillation on a wiped wall still, at a wall temperature of 45° and pressure of $1.5 \times 10^{-2}$ mbar, giving 644 parts (65.6%) of ethyl diethoxymethylphosphinate of 98.5% purity.

EXAMPLE 2

Using the procedure described in Example 1b, 363 parts of 90% aqueous phosphinic acid solution are reacted with 1930 parts of triethyl orthoformate in the presence of 114 parts of trifluoroacetic acid. Work up and purification by the procedures of Example 1b gives 631.5 parts (64.5%) of ethyl diethoxymethylphosphinate of 96.9% purity.

EXAMPLE 3

Using the procedure described in Example 1b, 3.3 parts of commercially available 50% aqueous phosphinic acid solution are reacted with 22.25 parts of triethylorthoformate in the presence of 0.57 parts of trifluoroacetic acid. Work up and purification by the procedures described in Example 1b gives 3.1 parts (62.9%) of ethyl diethoxymethylphosphinate of 94.7% purity.

EXAMPLE 4

Following the procedure set out in Example 1b, 7.31 parts of 90% w/w aqueous phosphinic acid are treated with 52.1 parts of tri-n-butylorthoformate in the presence of 1.14 parts of trifluoroacetic acid.

After purification by distillation, 16.0 parts of n-butyl di-n-butoxymethylphosphinate (58% yield of theory) are obtained having a b.p of 85° (at $3.3 \times 10^{-1}$ mbar) of 90% purity.

EXAMPLE 5

Following the procedure set out in Example 1b, 3.3 parts of 90% w/w aqueous phosphinic acid are reacted with 16.3 parts of triethylorthoformate in the presence of 0.96 parts of methane sulphonic acid to give ethyldiethoxymethylphosphinate (61.5% by $-$P nmr analysis).

EXAMPLE 6

Following the procedure set out in Example 1b, 3.3 parts of 90% w/w aqueous phosphinic acid are reacted with 16.3 parts of triethylorthoformate in the presence of 1.48 parts of p-toluene sulphonic acid to give ethyldiethoxymethylphosphinate (69.5% by $^{31}$P nmr analysis).

EXAMPLE 7

Following the procedure set out in Example 1b, 3.75 parts of 90% w/w aqueous phosphinic acid are reacted with 20.0 parts of triethylorthoformate in the presence of 1.42 parts of boron trifluoride etherate to give ethyldiethoxymethylphosphinate (56.2% by $-$P nmr analysis).

EXAMPLE 8

1908 parts (11.76 moles) of triethylorthoacetate are charged to a 5 liter reaction vessel and stirred while argon is passed through. The charge is cooled to 10° C. and 53.2 parts (0.375 mole) of boron trifluoride etherate are added, dropwise, over 15 minutes, maintaining the temperature at 10° C. When the addition is complete, the mixture is cooled further to 0°–b 5° C., and 178.7 parts (2.5 moles) of 92.3% phosphinic acid are added, dropwise, while maintaining the temperature at 0°–5° C. When this addition is complete, the reaction mixture is allowed to warm up to 20° C. and stirring is continued for 24 hours.

After 24 hours, 2650 parts of dichloromethane are added and the solution so obtained is added to a vigorously stirred solution of 147.7 parts (0.4125 mole) of disodium hydrogen orthophosphate dodecahydrate in 1100 parts water. The resulting two liquid phases are separated, and the aqueous phase is extracted with 650 parts of dichloromethane. The organic extracts are combined, and washed with 1000 parts water. The washed organic phase is dried over magnesium sulphate, filtered and the solvent is removed in vacuo. The crude product (517.2 parts) so obtained is distilled to give 338.5 parts (64.4% yield of theory) ethyl(1,1-diethoxyethyl)phosphinate as a colourless liquid having boiling point of 70° C. at $10^{-2}$ mbar, and the following analytical data; $^{31}$P-nmr $= +30.85$ ppm (CDCl$_3$) $^J$Ph$=539.8$ H$_2$

What is claimed is:

1. A novel process for the manufacture of alkyl dialkoxyalkylphosphinates of the formula I

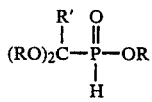

in which R is $C_1$–$C_4$-alkyl and R' is hydrogen or $C_1$–$C_4$alkyl, comprising reacting, in the presence of an acidic catalyst, aqueous phosphinic acid with the corresponding trialkyl orthoester having the formula II:

in which R and R' have their previous significances, the amount of the orthoester of formula II used being equal to, or in excess of the stoichiometric amount of both water and phosphinic acid present in the aqueous phosphinic acid reactant.

2. A process according to claim 1, wherein the aqueous phosphinic acid used contains 50 to 95% by weight of phosphinic acid.

3. A process according to claim 1, wherein the amount of orthoester reactant of formula II used is from 1 to 10 times the stoichiometric amount of both water and phosphinic acid present in the aqueous phosphinic acid reactant.

4. A process according to claim 1, wherein the amount of orthoester reactant of formula II used is from 1.0 to 5 times the stoichiometric amount of both water and phosphinic acid present in the aqueous phosphinic acid reactant.

5. A process according to claim 1, wherein the amount of orthoformate reactant of formula II used is from 2.2 to 4.4 times the stoichiometric amount of both water and phosphinic acid present in the aqueous phosphinic acid reactant.

6. A process according to claim 1, wherein the acidic catalyst is a mineralic acid, an alkane- or benzenesulfonic acid or an α-halogenated alkanoic acid.

7. A process according to claim 1, wherein the acidic catalyst is trifluoroacetic acid or boron trifluoride etherate.

8. A process according to claim 1, wherein 0.01 to 0.4, acid-equivalents of the acidic catalyst is applied.

9. A process according to claim 1, wherein 0.05 to 0.3, acid-equivalents of the acidic catalyst is applied.

10. A process according to claim 1, wherein the reactant of formula II is selected from
trimethyl orthoacetate,
trimethyl orthoformate,
triethyl orthoacetate,
triethyl orthoformate,
tri-n-propyl orthoacetate,
tri-n-propyl orthoformate,
tri-n-butyl orthoacetate and
tri-n-butyl orthoformate.

* * * * *